US00PP19390P2

(12) United States Plant Patent
Robb

(10) Patent No.: US PP19,390 P2
(45) Date of Patent: Oct. 28, 2008

(54) ***PHOTINIA* PLANT NAMED 'PARSUR'**

(50) Latin Name: *Photinia glabra*
Varietal Denomination: Parsur

(75) Inventor: John Robb, Kulnurra (AU)

(73) Assignee: The Paradise Seed Company Pty Ltd, Kulnurra (AU)

( * ) Notice: Subject to any disclaimer, the term of this patent is extended or adjusted under 35 U.S.C. 154(b) by 0 days.

(21) Appl. No.: 11/728,169

(22) Filed: Mar. 24, 2007

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent L. Bell
*Assistant Examiner*—Georgia Helmer

(57) ABSTRACT

A new and distinct cultivar of *Photinia* plant named 'Parsur' characterized by its upright and outwardly spreading plant habit; dark reddish brown stem coloration; leaves that are brown when developing and green when fully expanded; and undulating leaves with serrulate margins.

1 Drawing Sheet

Botanical Classification: *Photinia glabra.*
Variety denomination: 'Parsur'.

BACKGROUND OF THE INVENTION

The present Invention relates to a new and distinct cultivar of *Photinia* plant, botanically known as *Photinia glabra,* and hereinafter referred to by the name 'Parsur'. The new *Photinia* is a product of a planned breeding program conducted by the Inventor in Kulnurra, NSW Australia. The objective of the breeding program was to develop new *Photinia* cultivars with attractive habit and foliage.

The new cultivar originated from open pollination with *Photinia* 'Red Robin' (not patented) as the female parent with an unknown male parent in 2000. The cultivar 'Parsur' was discovered and selected by the Inventor in 2001 as a single plant within the progeny. 'Parsur' was discovered in an outdoor field from plants that were started in a greenhouse and then transplanted outdoors.

The first asexual reproduction of the new *Photinia* was in 2001 by terminal cuttings taken at Kulnurra, Australia. The unique features of this new *Photinia* are stable and reproduced true to type in successive generations of asexual reproduction.

SUMMARY OF THE INVENTION

The following traits have been repeatedly observed and are determined to be the unique characteristics of 'Parsur'. These characteristics in combination distinguish 'Parsur' as a new and distinct cultivar:

1. An upright plant habit.
2. Greyed-Purple stem coloration.
3. Leaves that are greyed-red when developing and green when fully expanded.
4. Medium to strong undulating leaves with serrulate margins.
5. Leaf shape oblong.

The closest comparison cultivar is the female parent 'Red Robin'. Plants of the new *Photinia* were compared to plants of the *Photinia* cultivar 'Red Robin'. In side-by-side comparisons conducted in Kulnurra, Australia, plants of the new *Photinia* differed from plants of the cultivar 'Red Robin' in the following characteristics:

1. Plants of the new *Photinia* had more lateral branches than 'Red Robin'.
2. Plants of the new *Photinia* had a more upright habit than 'Red Robin'.
3. Plants of the new *Photinia* have elliptic-slightly obovate leaves while 'Red Robin' has oblanceolate shaped leaves.
4. Plants of the new *Photinia* have darker leaves than 'Red Robin'.
5. Plants of the new *Photinia* have shorter leaves than 'Red Robin'.

| Characteristic | Parsur | Red Robin |
|---|---|---|
| Branching Strength | Medium | Weak |
| # of lateral branches | 8 | 4 |
| Colour young shoot | 183A | 183A |
| Undulation of margin | Strong | Weak |
| Mature leaf blade length | 100 mm | 126 mm |
| Mature leaf blade width | 32 mm | 50 mm |
| Length to width ratio | 3.1 | 2.5 |
| Shape of apex | Obtuse | Apiculate |
| Mature leaf undulation of margin | Strong | Weak |
| Petiole length | 10 mm | 20 mm |

BRIEF DESCRIPTION OF THE PHOTOGRAPHS

The accompanying photographs illustrate the distinguishing traits of *Photinia* 'Parsur'.

The photograph at the top of the sheet is a side view of a 2 year old plant.

The photograph at the bottom of the sheet is a close-up view of several leaves.

The photographs were taken using conventional techniques and although colors may appear different from actual colors due to light reflectance it is as accurate as possible by conventional photographic techniques.

DETAILED BOTANICAL DESCRIPTION

The new *Photinia* has not been observed under all possible environmental conditions. The phenotype may vary somewhat with variations in environment such as temperature and light intensity, without, however, any variance in genotype. The following is a detailed description of the new *Photinia* cultivar named 'Parsur'. Data was collected Kulnura, NSW Australia from plants raised in 200 mm pots in commercial grade, soilless potting mix in full sun. The plants were grown on their own roots from cuttings. In the following description, color references are made to The Royal Horticultural Society Colour Chart, 1995 Edition.

Botanical classification: *Photinia glabra* cultivar 'Parsur'.
Parentage:
Female parent: *Photinia* 'Red Robin'.
Male parent: Unknown.
Propagation: Terminal cuttings.
Time to initiate roots: About 60 days at 20 degrees Centigrade.
Time to produce a rooted young plant: About 120 days at 20 degrees Centigrade.
Root description: Medium thickness; dark brown in color.
Plant description:
Plant form: Upright perennial evergreen shrub.
Growth habit: Vigorous. Dense and bushy growth habit.
Plant height: 4 m.
Plant width: About 2 m.
Lateral branches: Quantity per plant: About 8. Diameter: About 4 mm. Internode length: About 3.2 cm. Strength: Strong. Texture: Smooth. Color: 185A to 179A.
Foliage description: Stems: Color Greyed-Purple 181A; diameter 5 mm. Leaves: alternate, single, and generally symmetrical. Length: About 87 mm. Width: About 47 mm. Shape: oblong. Apex: apiculate. Base: Obtuse-cuneate. Margin: Serrulate; lightly undulating.
Texture: Glabrous; leathery. Venation pattern: Pinnate. Color: Immature leaves, upper surface: 181A; lower surface: 185C. Mature leaves, upper surface: 135B; lower surface 143C. Petiole: Length: About 7.1 mm. Diameter: About 2–3 mm. Stipules: Quantity per leaf: Two. Arrangement/appearance: One stipule on either side of the base of the petiole; scale-like. Length: About 7.2 mm. Color: Upper surface: Green flushed red 147A.
Flower description: Flowers have not been observed.
Seed description: Seed production has not been observed.
Disease/pest resistance: In comparison to other known *Photinia* cultivars, plants of the new *Photinia* have been observed to be relatively more resistant to pathogens and pests common to *Photinia*.
Temperature tolerance: Plants of the new *Photinia* have been observed to tolerate temperatures ranging from −15 to 43 degree. C.

What is claimed is:

1. A new and distinct variety of *Photinia* plant named 'Parsur', as described and illustrated.

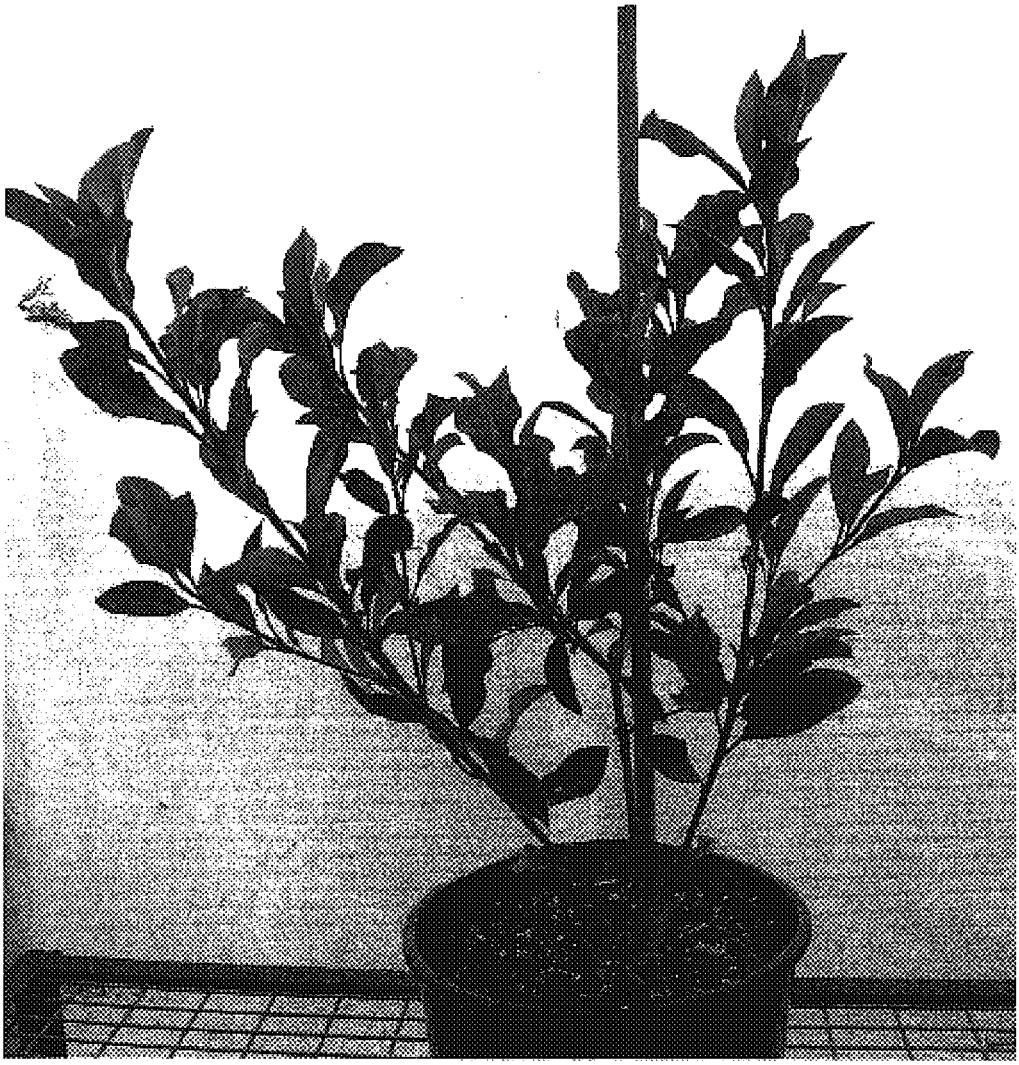
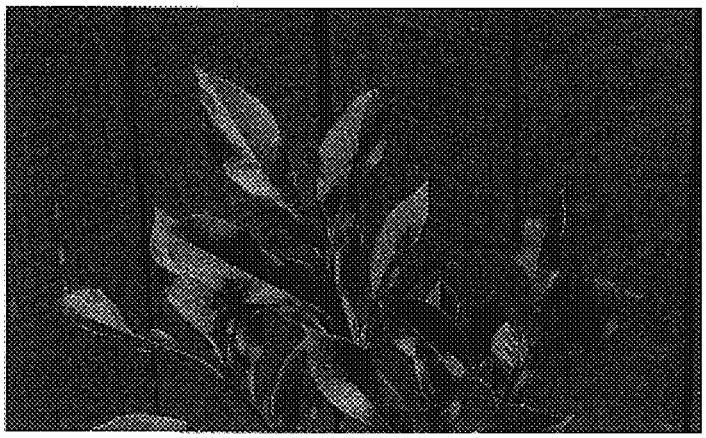

* * * * *